(12) United States Patent
Baumann et al.

(10) Patent No.: US 7,413,305 B2
(45) Date of Patent: Aug. 19, 2008

(54) OPHTHALMOLOGIC APPARATUS AND RELATED POSITIONING METHOD

(75) Inventors: Oliver Baumann, Aalen (DE); Michael Claus, Aalen (DE); Axel Doering, Jena (DE); Ingo Koschmieder, Jena (DE); Thomas Schulze, Oberkochen (DE); Bernd Spruck, Moegglingen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 10/533,394

(22) PCT Filed: Oct. 28, 2003

(86) PCT No.: PCT/EP03/11925

§ 371 (c)(1),
(2), (4) Date: Nov. 23, 2005

(87) PCT Pub. No.: WO2004/037077

PCT Pub. Date: May 6, 2004

(65) Prior Publication Data

US 2006/0146283 A1    Jul. 6, 2006

(30) Foreign Application Priority Data

Oct. 28, 2002   (DE) ............................... 102 50 569

(51) Int. Cl.
*A61B 3/14* (2006.01)
*A61B 3/10* (2006.01)

(52) U.S. Cl. ...................... 351/208; 351/209; 351/216; 351/221

(58) Field of Classification Search ................ 351/206, 351/208–209, 237, 211, 216
See application file for complete search history.

(56) References Cited

U.S. PATENT DOCUMENTS 5,098,426 A * 3/1992 Sklar et al. ..................... 606/5
5,430,507 A * 7/1995 Nishio et al. ................ 351/208
5,530,587 A * 6/1996 Sander et al. ............... 359/376

(Continued)

FOREIGN PATENT DOCUMENTS

DE    101 08 797    9/2002

(Continued)

*Primary Examiner*—Jordan M Schwartz
(74) *Attorney, Agent, or Firm*—Reed Smith LLP

(57) ABSTRACT

An arrangement and method for positioning an ophthalmologic device with respect to the patient's eye to be examined in x-, y- and/or z-coordinates. The device includes a controllable illumination unit, an observation system, an image recording unit, a central control unit, an output unit, an eye tracker unit, and a device for relative positioning. The imaging system of the eye tracker unit has at least two different adjustable magnifications. In positioning the ophthalmologic device, the signal of the eye tracker unit is used to track a measuring mark and/or grid structure projected on the eye, and also to detect the position of the patient's eye with respect to the optical axis of the ophthalmologic device. The inventive solution makes it possible to automatically position the entire device with respect to the eye to be examined, thus simplifying examination and accelerating determination of biometric data.

10 Claims, 2 Drawing Sheets

U.S. PATENT DOCUMENTS

| | | | |
|---|---|---|---|
| 5,548,354 A * | 8/1996 | Kasahara et al. | 351/206 |
| 5,889,576 A * | 3/1999 | Fujieda | 351/208 |
| 5,909,269 A * | 6/1999 | Isogai et al. | 351/208 |
| 5,943,116 A * | 8/1999 | Zeimer | 351/221 |
| 6,145,990 A | 11/2000 | Uchida | |
| 6,157,855 A * | 12/2000 | Sjoholm | 600/427 |
| 6,220,706 B1 | 4/2001 | Foley | |
| 6,280,436 B1 | 8/2001 | Freeman et al. | |
| 6,286,958 B1 * | 9/2001 | Koest et al. | 351/214 |
| 6,394,602 B1 * | 5/2002 | Morrison et al. | 351/206 |
| 6,702,809 B1 * | 3/2004 | Knopp et al. | 606/10 |
| 2002/0013573 A1 | 1/2002 | Telfair et al. | |
| 2002/0131017 A1 * | 9/2002 | Kishida et al. | 351/206 |
| 2003/0225398 A1 * | 12/2003 | Zepkin et al. | 606/4 |
| 2006/0158639 A1 * | 7/2006 | Campin et al. | 356/29 |

FOREIGN PATENT DOCUMENTS

| | | |
|---|---|---|
| EP | 11 088 511 | 4/2001 |
| WO | 99/27412 | 6/1999 |
| WO | 00/26713 | 5/2000 |

* cited by examiner

OPHTHALMOLOGIC APPARATUS AND RELATED POSITIONING METHOD

CROSS-REFERENCE TO RELATED APPLICATIONS

This application claims priority of International Application No. PCT/EP2003/011925, filed Oct. 28, 2003 and German Application No. 102 50 569.1, filed Oct. 28, 2002 the complete disclosures of which are hereby incorporated by reference.

BACKGROUND OF THE INVENTION a) Field of the Invention

The present invention is directed to an arrangement and method for automatic positioning of the device with respect to the patient's eye to be examined in the x, y and/or z coordinates. This method can advantageously be used to facilitate the determination of biometric data of the eye and other adjustments relating to diagnostics and therapy based on manual or stored method sequences. Data from an examination can be stored in order to examine the corresponding regions in another, subsequent examination under the same conditions so that changes can be determined.

b) Description of the Related Art

Technical solutions in which an ophthalmologic device is positioned semi-automatically or fully automatically on the eye to be examined after detection of the eye are already known from the prior art.

Patent EP 1 088 511 describes an ophthalmologic device which has a positioning unit for orientation of the measuring unit with respect to the eye to be examined. For this purpose, a detection unit which determines the relative position of the measurement unit with respect to the eye and monitors this position during measurement is provided. The determined measurement values are stored or rejected depending on the eye position determined by the detection unit. In this way, only measurements that were recorded when the eye was accurately positioned are processed and stored. This solution is disadvantageous compared with the method suggested in the present application due to the fact that the measurement unit of the ophthalmologic device must be roughly oriented by the user by means of a joystick at the start of the examination, i.e., when the patient sits in front of the device and the patient's eye has been brought into a fixed position. The detection unit cannot determine the position of the eye and send the corresponding signals to the positioning unit for fine adjustment until after this rough adjustment. In other words, the process is subject to subjective influences such as the experience of the user in adjusting.

An automatically aligning optometric measurement device and the method for its use are described in U.S. Pat. No. 6,145,990. This solution has means for projecting a light mark on the eye, means for evaluating corneal reflex images, and means for controlling the actuating drives for exact positioning of the optometric measurement device. Positioning is carried out in all three coordinate directions for the first eye and then for the second eye based on the position of two light marks relative to one another, these light marks being generated from the corneal reflex image. After positioning, the corresponding measurements are carried out on the eye. Depending on whether or not the measurement is successfully carried out, a new measurement is carried out or the device is positioned on the other eye.

In the solution described in U.S. Pat. No. 6,220,706, the position of the eyes is likewise determined by illuminating the eyes and subsequently evaluating the reflected beam. For this purpose, two pairs of radiation emitter-photodetectors are arranged lateral to the eye in such a way that a radiation emitter and a photodetector of different pairs are located on each side of the eye. The photodetectors receive the radiation that is emitted by the respective associated radiation emitter and reflected by the eye. A controller analyzes the data of the photodetectors, which are constructed as 4-quadrant photodetectors, in order to determine the exact position of the eye. This technical solution determines, in particular, the focus position, i.e., the exact distance of the eye from the optics of the device.

The known technical solutions have the disadvantage that exact alignment of the measurement device to the eye either depends subjectively upon the user in the absence of automatic positioning or that additional technical devices are always required when automatic positioning is provided, which makes the overall device substantially more complicated and harder to oversee.

OBJECT AND SUMMARY OF THE INVENTION

It is the primary object of the present invention to develop an ophthalmologic device and a method for control thereof in which sources of subjective errors are minimized in the alignment of the device to the optical axis of the eye so that the measurements to be determined are exact and reliable. The user is no longer required to make a rough adjustment. The device is not substantially more complicated with respect to its construction and applicability.

According to the invention, this object is met by an ophthalmologic device comprising a controllable illumination unit, an observation system, an image recording unit, a central control unit, an eye tracker unit and means for relative positioning of the ophthalmologic device with respect to the eye to be examined. The eye tracker unit includes an imaging system. The imaging system has at least two different adjustable magnifications.

The ophthalmologic device for determining biometric data of an eye has many applications both in medicine and in optometry. A significant savings in time is achieved due to the automatic positioning. In some ophthalmologic devices, light marks and light patterns are already tracked by eye tracker units for eye movement, so that their use for eye detection does not represent an increased cost or further complication of technical apparatus.

The invention will be described more fully in the following with reference to an embodiment example.

DESCRIPTION OF THE PREFERRED EMBODIMENTS

Figure 1:
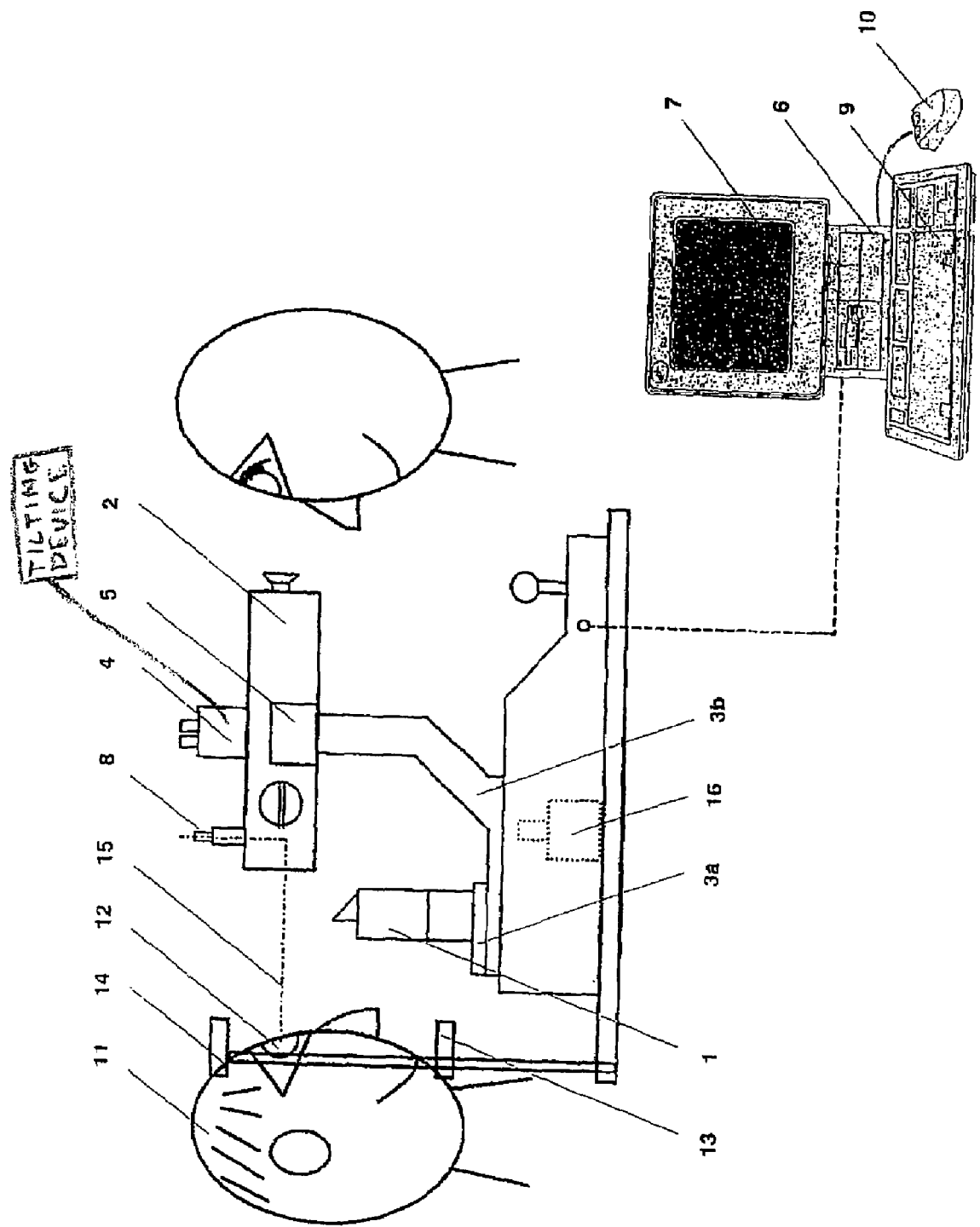
FIG. 1 is a schematic view of an ophthalmologic device with positioning means.

An ophthalmologic device, for example, for determining biometric data of an eye, is shown schematically in FIG. 1 and comprises a preferably digitally controllable illumination unit 1 and, as observation system, a stereo microscope 2 with different magnifications that are arranged on separate supporting arms 3a and 3b so as to be swivelable independent of one another. A special eye tracker unit 8 is connected to an associated IR illumination unit, which works in synchronization with the image rate of the eye tracker unit 8, and a central control unit 6 for detecting, processing and storing data. The IR illumination ensures that no influence can be exerted with the actual high-resolution digital recording camera in the VIS range. The camera beam path and eye tracker beam path are accordingly optically separated with respect to spectrum and cannot influence one another. A suitable IR bandpass filter that is transparent only for the light of the IR illumination unit is provided for support of the eye tracker unit 8. On the other hand, an IR cut filter is provided for the digital illumination unit 1 so that no IR light is emitted. The high-resolution digital camera and eye tracker unit 8 are coupled in by means of one or more input-coupling system(s) 5. The central control unit 6 has a user interface and has connections to a monitor 7 and/or printer serving as an output unit and to an eye tracker unit 8 as well as to means for relative positioning of the ophthalmologic device with respect to the eye 12 of the patient 11. For this purpose, the eye tracker unit 8 has an imaging system with at least two settings for different aperture angles. The control unit 6 further has a user interface with input devices such as keyboard 9, mouse 10, trackball, joystick, or the like, by means of which different control modes and evaluating modes can be called up.

The image recording unit 4 advantageously has a device for inclining the camera chip relative to the optical axis 15 for Scheimpflug correction and is capable of recording image sequences.

Figure 2:
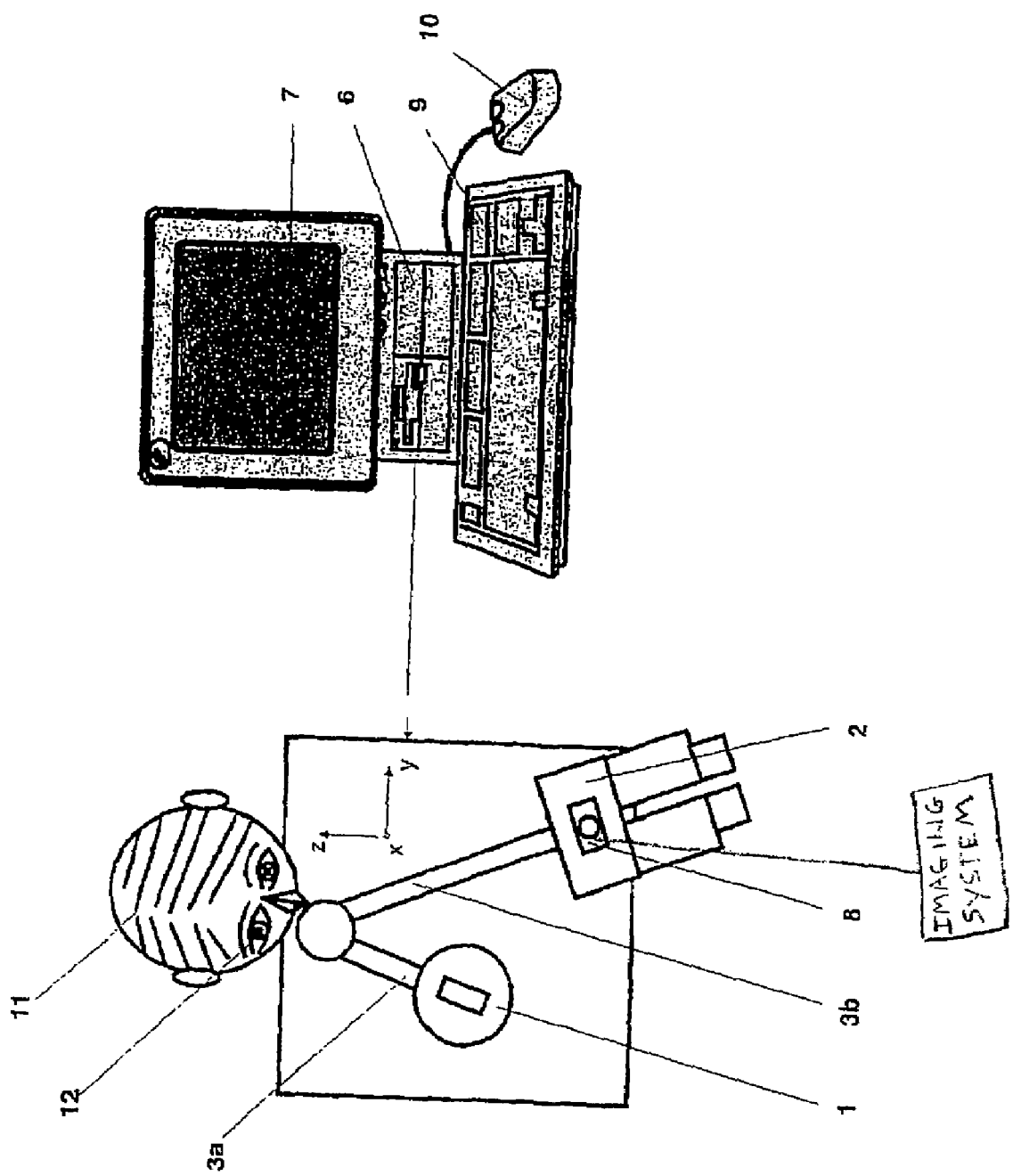
FIG. 2 is a corresponding schematic top view.

FIG. 2 shows a schematic top view of a slit lamp with means for positioning the device. In the method for positioning an ophthalmologic device with respect to the eye 12 to be examined, the signal of the eye tracker unit 8 is used not only to track a measurement mark and/or grid structure projected on the eye 12 but also to detect the position of the eye 12 being examined with reference to the optical axis 15 of the ophthalmologic device.

To examine or determine biometric data, the eye 12 of the patient 11 is brought to a fixed position by means of the provided chin rest 13 and forehead support 14. The eye tracker unit 8 comprises a camera and IR illumination which is coupled in, e.g., by a beam splitter. The uniform field projected on the eye 12 by the IR illumination is reflected by the eye and generates an image of the eye 12. When the wide-angle setting of its objective is selected, the eye tracker unit 8 supplies signals in evaluation of this image which exactly define the position of the pupil center. For this purpose, the objective has a correspondingly large aperture angle of about 45° at a distance of about 100 mm from the eye 12.

These coordinates obtained from the signals define the position of the patient's eye 12 relative to the eye tracker unit 8 and therefore also relative to the optical axis of the ophthalmologic device itself with reference to the x-plane and y-plane. A corresponding reference value is generated from these signals by the central control unit 6 with respect to amount and direction for the positioning unit and is supplied to the latter. The actuating drives are controlled based on the reference value. For exact positioning of the ophthalmologic device with respect to an eye 12 to be examined, it is advantageous when an actuating drive 16 is provided for each of the three coordinate directions. The difference between the center of the eye 12 and the optical axis 15 of the ophthalmologic device is zeroed by relative movement and continuous monitoring by the eye tracker unit 8. This is possible because the eye tracker unit 8 has a high measurement repetition rate and supplies the exact coordinates of the pupil center multiple times per second. After alignment in x- and y-direction, the objective setting of the imaging system of the eye tracker unit 8 can be changed in order to take over the tracking of patterns on the eye with higher accuracy, for example. This can be carried out, e.g., by means of changing the objective or zoom setting automatically or manually. The ophthalmologic device is now ready for the following measurements and examinations and/or treatment of the eye 12. When the objective setting of the imaging system of the eye tracker unit 8 is changed, the actuating drives 16 are deactivated at the same time.

However, it is also possible to carry out alignment in z-direction. The method according to U.S. Pat. No. 6,220,706, for example, can be applied for this purpose.

The eye tracker unit 8 is advisably connected to the optical axis 15 of the observation system 2 so that a possible parallax need not be taken into account.

After the eye 12 of the patient 11 has been brought to a fixed position, it is advantageous when the positioning process is triggered by a selector button, a pulse transmitter at the forehead support 14, chin rest 15, or the like. Further, after examining and/or measuring one eye of the patient, it is possible to position the ophthalmologic device on the other eye of the patient automatically or by pressing a button.

After treatment of a patient, the ophthalmologic device can be moved into a basic position. For the next patient, the device is either aligned automatically to the first eye to be examined or instructions are given to the control unit about which eye is to be positioned on. However, it is also conceivable for the ophthalmologic device to remain in the final position after treatment of a patient. Instructions can be given to the control unit about which eye to align to for the next patient or the examination starts with the last eye examined for the previous patient.

The solution proposed with the ophthalmologic device according to the invention makes it possible to automatically position the entire device with respect to the eye to be examined. The examination and determination of the biometric data of an eye can be simplified and substantially accelerated in this way. Apart from the actuating drives, no other technical apparatus is required, so that the overall construction of the device is not made more complicated or difficult to oversee. The ophthalmologic device can also conceivably be a fundus camera or slit lamp, for example.

While the foregoing description and drawings represent the present invention, it will be obvious to those skilled in the art that various changes may be made therein without departing from the true spirit and scope of the present invention.

REFERENCE NUMBERS

1 illumination unit
2 stereo microscope
3a, 3b supporting arm
4 image recording unit
5 optical input-coupling system
6 central control unit
7 monitor
8 eye tracker unit
9 keyboard
10 mouse
11 patient
12 eye to be examined
13 chin rest
14 forehead support
15 optical axis
16 actuating drive

The invention claimed is:

1. An ophthalmologic device comprising:
   a controllable illumination unit;
   an observation system;
   an image recording unit;
   a central control unit;
   an output unit;
   an eye tracker unit; and
   means for relative positioning of the ophthalmologic device with respect to the eye to be examined before any measurement examination and/or treatment is carried out; and
   wherein the eye tracker unit includes an imaging system, said imaging system having at least two different adjustable magnifications, a first magnification for determining a position of the eye relative to the optical axis and a second magnification to track a pattern of projected light marks on the eye.

2. The ophthalmologic device according to claim 1, wherein the imaging system of the eye tracker unit is a zoom objective or an interchangeable objective.

3. The ophthalmologic device according to claim 1, wherein the image recording unit comprises a digital high-resolution camera with a high image rate which can have a tilting device for tilting the camera chip relative to the optical axis for Scheimpflug correction and/or is capable of recording and storing image sequences.

4. The ophthalmologic device according to claim 3, wherein the image recording unit operates synchronously with the image rate of the digital high resolution camera.

5. The ophthalmologic device according to claim 1, wherein the central control unit has a user interface with conventional input devices and/or has different controlling and evaluating modes.

6. The ophthalmologic device according to claim 1, wherein the output unit is a monitor and/or printer.

7. A method for positioning an ophthalmologic device, comprising the steps of:
   bringing the patient's eye to a fixed position by an existing chin rest and forehead support;
   selecting a wide-angle setting of the imaging system of an eye tracker unit;
   said eye tracker unit with said wide-angle setting of the imaging system supplying signals containing the coordinates of the eye relative to the eye tracker unit and, therefore, also relative to the optical axis of the ophthalmologic device;
   said eye tracker unit generating a corresponding reference value from these signals with respect to amount of movement and direction for a positioning device;
   said eye tracker unit also supplying a reference signal to the positioning device;
   carrying out an alignment by continuous detection of the eye position and relative movement; and
   changing the magnification of the imaging system of the eye tracker unit after alignment in x-direction and y-direction.

8. A method for positioning an ophthalmologic device, comprising the steps of:
   bringing the patient's eye to a fixed position by an existing chin rest and forehead support;
   selecting a wide-angle setting of an objective of a stereo microscope of the image recording unit;
   said image recording unit supplying signals containing the coordinates of the eye relative to the image recording unit and, therefore, also relative to the optical axis of the ophthalmologic device;
   said image recording unit generating a corresponding reference value from these signals with respect to amount of movement and direction for the positioning device; and
   said image recording unit also supplying this a reference signal to the positioning device;
   carrying out an alignment by continuous detection of the eye position and relative movement; and
   changing the objective setting of the stereo microscope after alignment in x-direction and y-direction.

9. The method for positioning an ophthalmologic device according to claim 7,
   wherein an alignment of the ophthalmologic device in z-direction is carried out after alignment has been carried out in x-direction and y-direction and after the aperture angle of the imaging system of the eye tracker unit has been changed.

10. The method for positioning an ophthalmologic device according to claim 7, further comprising evaluating an image of the eye generated by illumination and further comprising the eye tracker unit tracker patterns of projected light marks on the eye wherein detection of the eye by the eye tracker unit is carried out in such a way that in evaluating the image of the eye generated by illumination, the pupil center is exactly determined and the tracking Of the light marks is carried out by continuous detection of the pupil by the eye tracker unit.

* * * * *